US009265684B2

(12) United States Patent
Seger

(10) Patent No.: US 9,265,684 B2
(45) Date of Patent: Feb. 23, 2016

(54) DESK AND RECOVERY SYSTEM

(71) Applicant: Daniel E. Seger, Hanover, MD (US)

(72) Inventor: Daniel E. Seger, Hanover, MD (US)

( * ) Notice: Subject to any disclaimer, the term of this patent is extended or adjusted under 35 U.S.C. 154(b) by 377 days.

(21) Appl. No.: 13/923,155

(22) Filed: Jun. 20, 2013

(65) Prior Publication Data

US 2013/0340766 A1 Dec. 26, 2013

Related U.S. Application Data

(60) Provisional application No. 61/662,261, filed on Jun. 20, 2012.

(51) Int. Cl.

| | |
|---|---|
| ***A61F 5/00*** | (2006.01) |
| ***A61G 99/00*** | (2006.01) |
| ***A61G 7/015*** | (2006.01) |
| ***A61G 7/065*** | (2006.01) |
| ***A61G 7/07*** | (2006.01) |
| ***A61G 7/075*** | (2006.01) |

(52) U.S. Cl.

CPC ................ *A61G 99/00* (2013.01); *A61G 7/015* (2013.01); *A61G 7/065* (2013.01); *A61G 7/07* (2013.01); *A61G 7/075* (2013.01); *A61G 2200/325* (2013.01); *A61G 2200/38* (2013.01)

(58) Field of Classification Search

CPC ........................................................ A61F 5/00
USPC ........ 5/610–613, 616; 128/845; 606/240, 242
See application file for complete search history.

(56) References Cited

U.S. PATENT DOCUMENTS

| | | | | |
|---|---|---|---|---|
| 2,091,014 | A * | 8/1937 | Saak | ............................ 606/244 |
| 2007/0290538 | A1 | 12/2007 | Walter | |
| 2008/0134434 | A1 | 6/2008 | Celauro | |

FOREIGN PATENT DOCUMENTS

| | | |
|---|---|---|
| WO | 2007059045 A | 5/2007 |
| WO | 2008057618 A | 5/2008 |

* cited by examiner

*Primary Examiner* — Fredrick Conley
(74) *Attorney, Agent, or Firm* — The Law Firm of Andrea Hence Evans, LLC

(57) ABSTRACT

The invention features a desk and recovery system that affords the user the ability to avoid stress and strain on the user's back, head and neck. The system features an upper body support featuring a torso or chest support which receives the stomach of the user for face-down support or face-down recovery. Adjustable arms are provided for an entertainment system, such as keyboard and monitor. The torso or chest, knee and buttocks supports can tilt, rotate and are height adjustable.

16 Claims, 6 Drawing Sheets

DESK AND RECOVERY SYSTEM

RELATED U.S. APPLICATION DATA

This application claims the benefit of provisional application No. 61/662,261, filed Jun. 20, 2012.

FIELD OF THE INVENTION

The present invention relates, in general, to a desk system which allows a user to lie down, providing minimal to no strain on the user's back.

BACKGROUND OF THE INVENTION

Most back pain is caused by mechanical problems with the joints and muscles of the back. Disorders of internal organs can also cause back pain. Strained muscles, inflammation of the nerves, poor posture, physical stress, loss of flexibility and scarring from previous injuries are common causes of back pain. To prevent further injury and relief from the pain, it is recommended that lying on the stomach in a face-down position can decrease back pain. After many surgeries, the patients are often required to lay face-down to recover and to avoid the recurrence of back pain.

After retinal surgery, such as a vitrectomy, face-down recovery or face-down positioning is essential for surgery recovery. Due to limited and restrictive recovery apparatus, face-down positioning is excruciating, boring, and stressful. During recovery, muscles ache, face swellings occur and entertainment and stimulation are limited.

SUMMARY OF THE INVENTION

The present invention provides an adjustable desk and recovery system that removes stress and strain from the user's back and provides entertainment and support.

An aspect of an embodiment of the invention provides a pin and hinge adjustment system which locks and unlocks the head, chest, knee and buttock supports enabling them to adjust in a horizontal, vertical or circular motion.

A further aspect of an embodiment of the invention features pivot points along the base of the supports which allow the supports to turn or oscillate to afford the system to be positioned in the best position for the user.

A further aspect of an embodiment of the invention features adjustable and extendable arms that support an entertainment system whereby the arms feature multiple pivot points so the arms can be extended vertically, horizontally or rotate and locked into position.

A further aspect of an embodiment of the invention features mirrors attached to the system to afford looking at surroundings without lifting the head or neck avoiding stress and strain on the head or neck.

A further aspect of an embodiment of the invention features collapsible arm rests which can extend out of the system to support the arms or into the system allowing the arms to be mobile.

Additional aspects, objectives, features and advantages of the present invention will become apparent from the following description of the preferred embodiments with reference to the attached drawings.

DETAILED DESCRIPTION OF THE INVENTION

Figure 1:
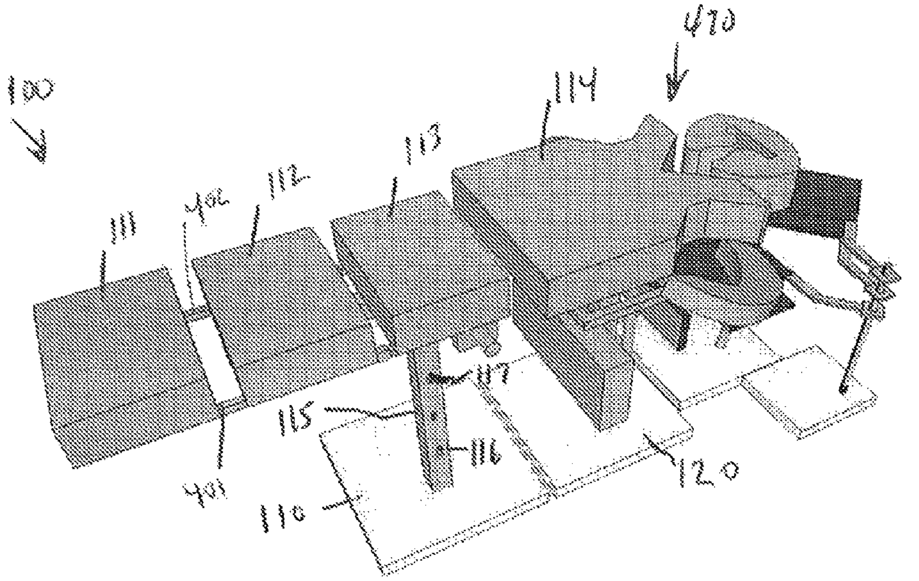
FIG. 1 is a perspective view of the desk and recovery system.

FIG. 1 is a perspective view of the desk and recovery system 100. The system 100 features a lower body platform 110 and an upper body platform 120. The platforms 110, 120 support the lower body supports 111, 112, 113 and the upper body support 114, respectively. An adjustable lower body base 115 is secured to the lower body platform 110. The adjustable lower body base 115 may be pushed in using a force or screwed into the lower body platform 110. Alternate attachment mechanisms may be used. The lower body supports 111, 112, 113 are attached to the lower body platform 110 so that their positioning and movement is independent from the upper body support 114. The adjustable lower body base 115 extends upwards from the lower body platform 110. The bottom of the lower body platform 110 contacts the ground surface. The lower body base 115 extends upwards from the top surface of the lower body platform 110. The lower body base 115 is adjustable in a vertical direction such that the height of the lower body base 115 can be adjusted. A pin and hinge adjustment system secures the base 115 at the desired height. The outside of the base 115 has openings 116 which can receive a pin 117. The pin 117 extends through the openings 116 and through the matching opening on the inside portion of the base 115, which will prevent the inside portion of the base 115 from moving in a vertical direction. When it is desired to lower the base 115 or move it to a different height, the pin is removed and placed in the desired opening.

Figure 3:
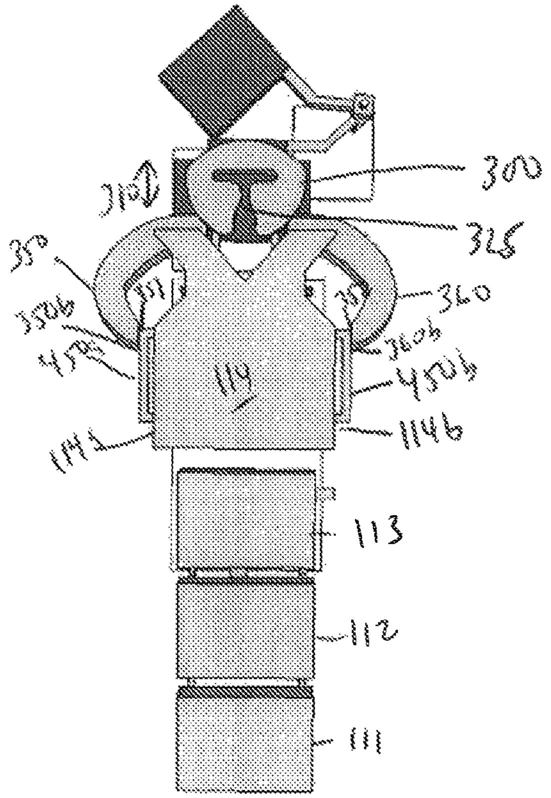
FIG. 3 is a top view of the desk and recovery system.
Figure 4:
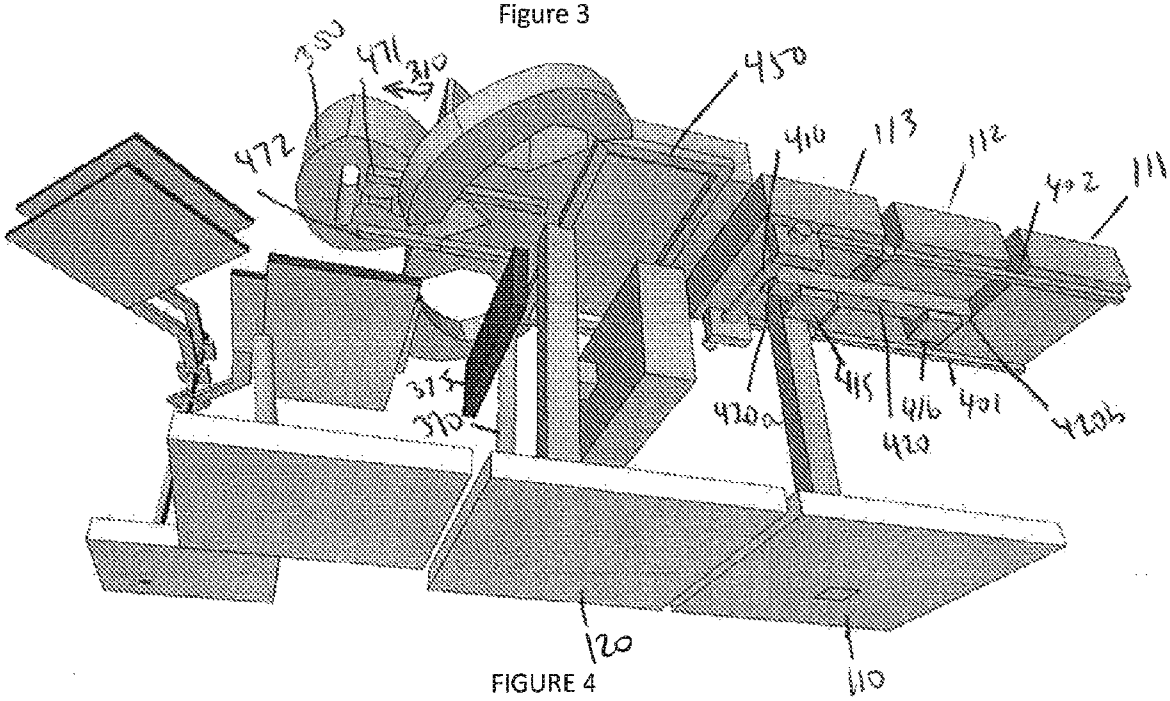
FIG. 4 is a bottom perspective view of the desk and recovery system.

A first and second lower body rail 401, 402 is connected to the lower body base 115, as shown in FIG. 4. FIG. 4 is a bottom perspective view of the desk and recovery system 100. The base 115 is perpendicular to the rails 401, 402. The rails 401, 402 are parallel to each other and spaced apart such that they receive and support the lower body supports 111, 112, 113. The rails 401, 402 contact the lower body supports 111, 112, 113 substantially near the edges of the lower body supports 111, 112, 113. The rails 401, 402 act as guides for the lower body supports 111, 112, 113. The supports 111,112, 113 slide along the rails independent of each other. For example, the supports 111, 112, 113 can be spaced apart, as shown in FIG. 3, to relieve pressure on different parts of the users lower body. FIG. 3 is a top view of the desk and recovery system 100. For example, if the user is taller, supports 111, 112, 113 can be spaced further apart from each other to support the user's body. Alternatively, additional supports may be added along the rail. Also, the supports can be sized to be wider or longer to support various body types. Alternatively, less supports can be positioned along the rails to support the user's lower body. The lower body support 113 supports the buttocks area of the user. The lower body support 112 supports the lower torso including the thigh area of the user. The lower body support 111 supports the calves and foot area of the user.

Figure 5:
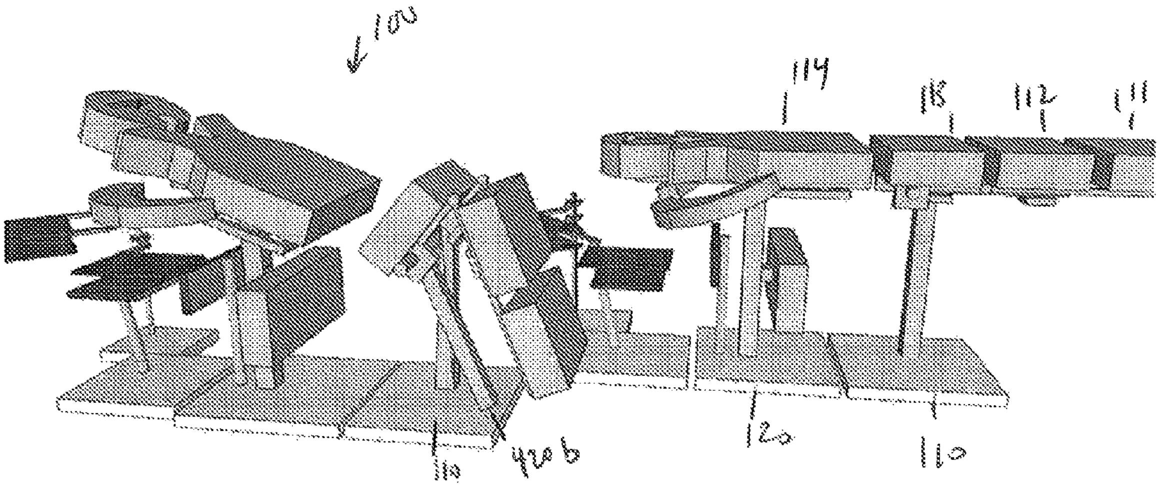
FIG. 5 is a perspective view of the desk and recovery system demonstrating the lower body support in a pivoted and horizontal position.
Figure 6:
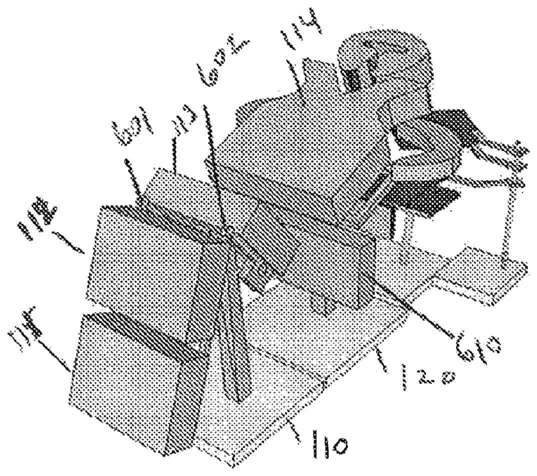
FIG. 6 is a perspective view of the desk and recovery system with the lower body support pivoted.

FIG. 6 is a perspective view of the desk and recovery system 100 with the lower body supports 111, 112, 113 pivoted. The lower body supports 111, 112, 113 can move from a horizontal position to an angled position to allow for blood flow of the user's body and to allow the user to be repositioned on the system 100. FIG. 5 is a perspective view of the desk and recovery system demonstrating the lower body support in a pivoted and horizontal position. Pivot points 601,602 are positioned along the lower body rails 401, 402. The lower body supports pivot and move along the lower body rails 401, 402. The pivot points 601, 602 are located along the rails 401, 402, respectively. The points 601, 602 are between the lower body support 113 and lower body support 112. The points 601, 602 act as a joint that allows the rail to move from a horizontal position to an angled position, along with the connected lower body supports. The points 601, 602 allow the rails and connected supports to move to a downward angle position so that the lower body support 113 is angled downwards towards the upper body support 114 and lower body supports 112 and 111 are angled downwards away from the upper body support 114. In this position, as shown in FIG. 6, the user's upper body can rest on the upper body support 114 and the user's buttocks will be rest on the lower body support 113. The user's knees will rest against the knee support 610. Although one set of pivot points 601, 602 are shown, an additional set of points can be positioned along the rails between the lower body support 112 and lower body support 111 so that the supports can pivot at an upwards or downwards angle to support the user's body. The supports are made of padding and cushion. Additional padding may be added to the supports to add extra cushion and comfort to the user's body parts.

Figure 2:
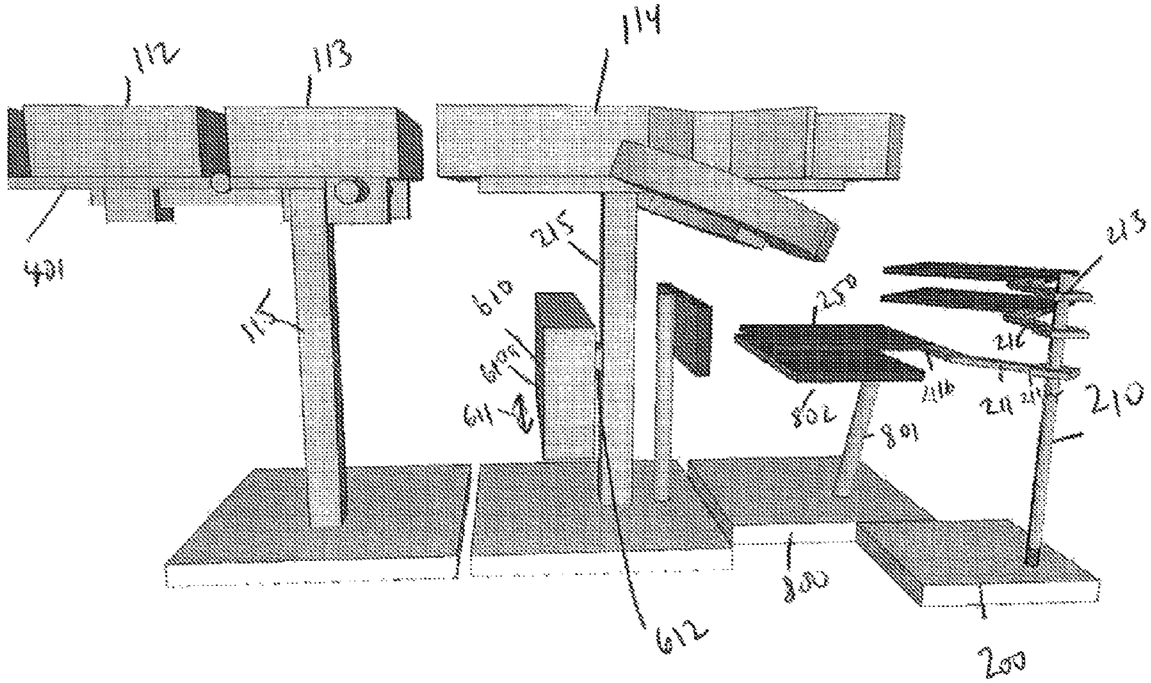
FIG. 2 is a side perspective view of the desk and recovery system.

The knee support 610 is on the adjustable upper body base 215. FIG. 2 is a side perspective view of the desk and recovery system 100. The knee support 610 is parallel to the adjustable lower body base 115 whereby the front of the user's knees will contact the front surface 610*a* of the knee support 610. The knee support 610 can be adjusted in a vertical direction 611. A knee rod 612 on the back side of the knee support 610 slides upwards and downwards along the inside front side of the adjustable upper body base 215 to move the knee support to its desired vertical position.

Figure 7:
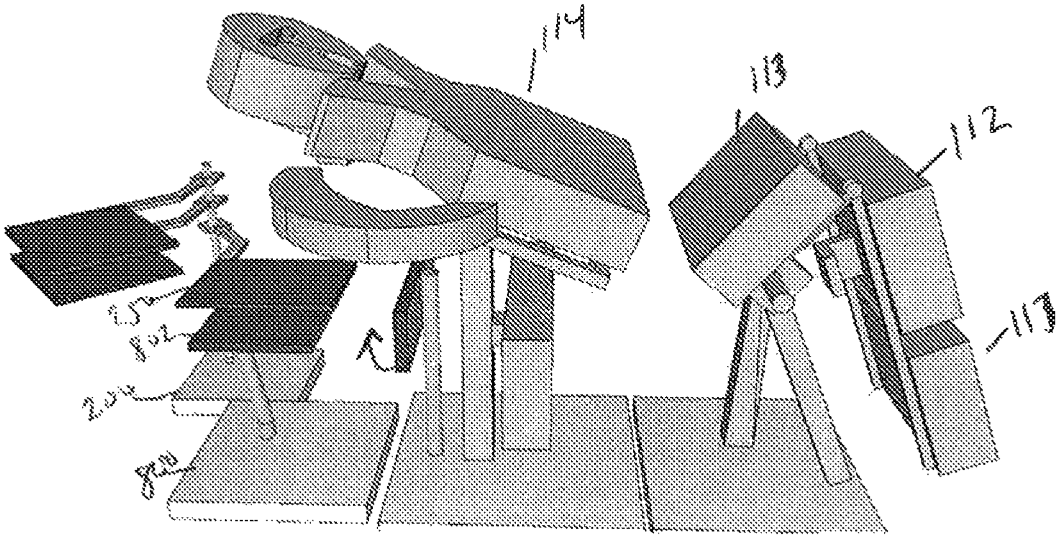
FIG. 7 is a side perspective view of the desk and recovery system with the lower body support pivoted.
Figure 8:
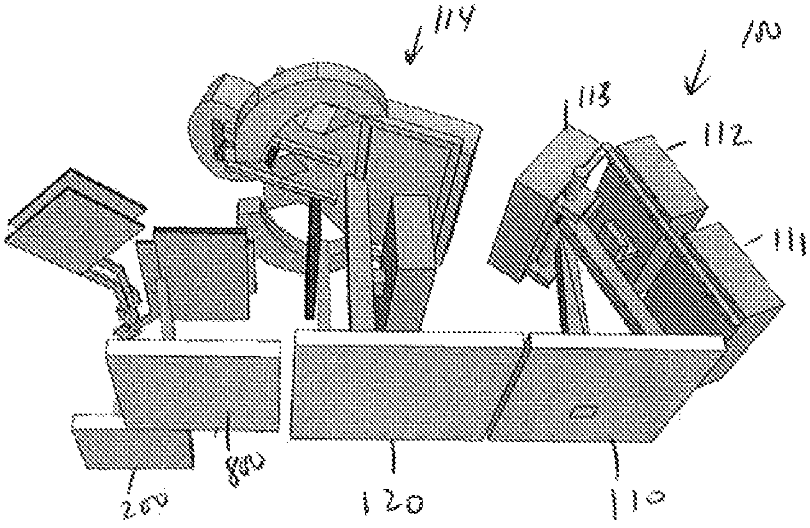
FIG. 8 is a bottom perspective view of the desk and recovery system with the lower body support pivoted.

FIG. 7 is a side perspective view of the desk and recovery system 100 with the lower body supports 111, 112, 113 pivoted. FIG. 8 is a bottom perspective view of the desk and recovery system 100 with the lower body supports 111, 112, 113 pivoted. A brace 410 is provided underneath the lower support 113 to provide extra support of the pad and to help to support the weight of the user. The brace 410 spans between the left and right edges of the support 113, between rails 401, 402. Additional braces may be added to provide additional support, if necessary. A first kickstand receiver 415 hangs underneath the lower body support 113. The first kickstand receiver 415 is C-shaped and the opening holds a first end 420*a* of kickstand brace 420 in an upwards position along the undersides of the lower body supports 113 and 112. A second kickstand receiver 416 hangs underneath the lower body support 112 and supports a second end 420*b* of the kickstand brace 420. When the lower body support 113 pivots along points 601, 602, the kickstand brace 420 is disconnected from the receivers 416 and 415 so that end 420*b* contacts the top surface of lower body platform 110, as shown in FIG. 5. The kickstand brace 420 is angled along the lower body platform 110 and the lower body base 115 remains at a right angle along the lower body base 115. The kickstand brace 420 provides additional support to the lower body support 113 as it is in the pivoted position.

The recovery system further comprises an upper body platform 120. An adjustable upper body base 215 extends upwards from the upper body platform. An adjustable upper body base 215 is secured to the upper body platform 120. The adjustable upper body base 215 may be pushed in using a force or screwed into the lower body platform 120. The bottom of the upper body platform 120 contacts the ground surface. The upper body base 215 is adjustable in a vertical direction such that the height of the upper body base 215 can be adjusted. An upper body support 114 is secured to the upper body base 215. The upper body support supports the shoulder area of the user, chest and stomach area of the user. The upper body support may be designed as one pad which receives most of the user's torso or multiple pads that can be adjusted to accommodate the length of the user's torso. The pads can be adjusted in a sliding motion towards or away from each other. A square bracket 450 is underneath the upper body support 114, as shown in FIG. 4. The square bracket 450 is larger than the area of the upper body support 114 so that the left 450*a* and right 450*b* sides of the bracket 450 extend further out from the left 114*a* and right 114*b* sides of the upper body support 114, as shown in FIG. 3. The left and right sides 450*a*, 450*b* of the bracket 450 can be gripped by the user to help them position their body in a desired position onto the system 100. Furthermore, the bracket 450 adds additional support to the upper body support 114 to support the additional weight of the user. The upper body support and lower body support move independently from each other.

The front area 470 of the upper body support 114 features head support rails 471, 472 which receive a head support 300. The head support 300 adjustable along the rails 471, 472 in a left and right direction shown by arrows 310. The head support 300 features a T-shaped opening 325 where the opening aligns with the eyes, nose and mouth area of the user on the system 100. The opening 325 also allows for ventilation and airflow to provide additional comfort to the user. The head support is a cushion is positioned near the top area of the head support base to support the head of the user. The rails below the head cushion allows the head cushion to slide in a vertical up and down direction or a left and right angled position. The head cushion may be in the form of a silk pillow for extra cushion and comfort and may have additional opening sin the center to allow ventilation exposing the user's nose and mouth. The opening in the pillow can be designed so only the forehead rests on the pillow.

A table base 370 near the front area of the upper body platform 120 extends upwards from the platform 120. A hinge along the top area of the table base 370 is connected to a table 375, shown in a rest position in FIG. 4. In a rest position, the table 375 is folded down. In a use position, the table moves upwards around the hinge in a direction shown by arrow 700, shown in FIG. 7. The top surface of the table 375 aligns with the opening 325. Thus, the user can view the top surface of the table and any objects placed on the top surface of the table while on the system 100.

The system further features a first arm support 350 and a second arm support 360. The back ends 350*b* and 360*b* are connected with a rotating gear to the front left edge 352 and left right edge 353 of the bracket 450, as shown in FIG. 3. The rotating gear allows the arm supports 350, 360 to adjust upwards or downwards along the edges of the bracket 450.

The recovery system comprises a desk platform 200, shown in FIG. 2. An adjustable desk base 210 is secured to the desk platform 200. The adjustable desk base 210 may be pushed in using a force or screwed into the desk platform 200.

Alternate attachment mechanisms may be used. The adjustable desk base extends upwards from the desk platform. Arms 211, 212, 213 are connected to the desk base 210. The first end 211*a* of the arm 211 is connected to a connector which has an opening that is received by the desk base 210. The opening is surrounded by edges that allow the opening and connected arm to swivel or rotate around the desk base 210. The second end 211*b* of the arm 211 is connected to a table 250. Arms 212 and 213 feature the same structure as arm 211 with ends and tables connected. The arm rests can extend out of the upper body support and support the arms of the user. The arm rests can be inserted and secured inside of the chest support, when not in use, or extended outside of the upper body support to allow the arms to be mobile and not supported or resting on the arm rests.

The tables can be positioned so that their top surface is aligned with the opening 325 of the head support 300. Objects or devices, for example can be placed on the surface of the tables and the user can easily rotate the table in a position so that it is aligned with the opening or in a position so that it is not aligned with the opening. The arms can hold the entertainment system. The entertainment system may be stereo system, laptop computer or a desktop computer with a monitor and separate keyboard, for example. The arms can be designed to have additional shelves extending out of them to separate the entertainment system or to provide additional areas to support objects such as books, cups or any personal items.

An additional table 802 supported by a base 803 and platform 800 is shown in FIG. 2 with one table. As discussed, the table can support any items desired by the user. The table can fold into a use and nonuse position as described above when the table is aligned with the opening 325.

Figure 9:
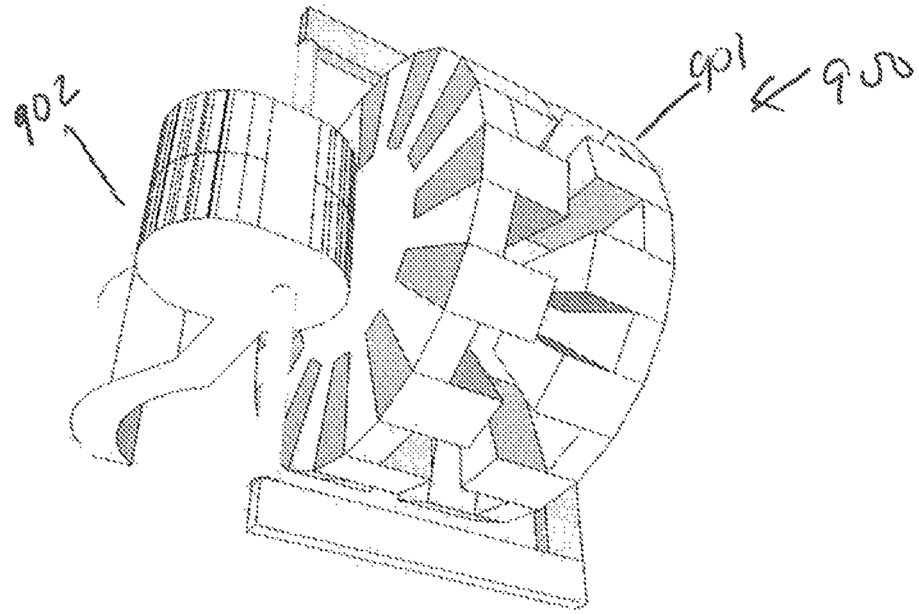
FIG. 9 is a perspective side view of the gear system of the desk and recovery system in an open position.
Figure 10:
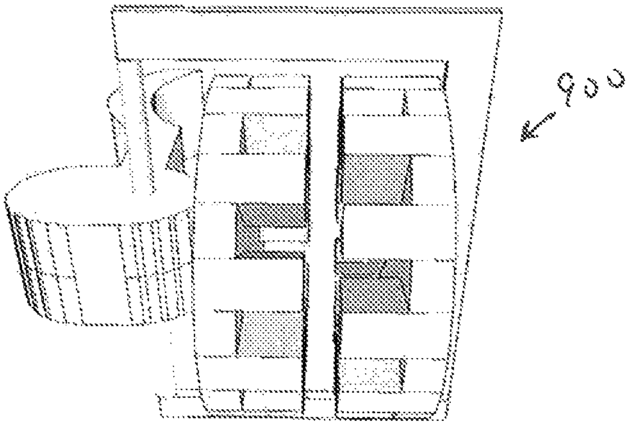
FIG. 10 is a front perspective view of the gear system of the desk and recovery system in an open position.
Figure 11:
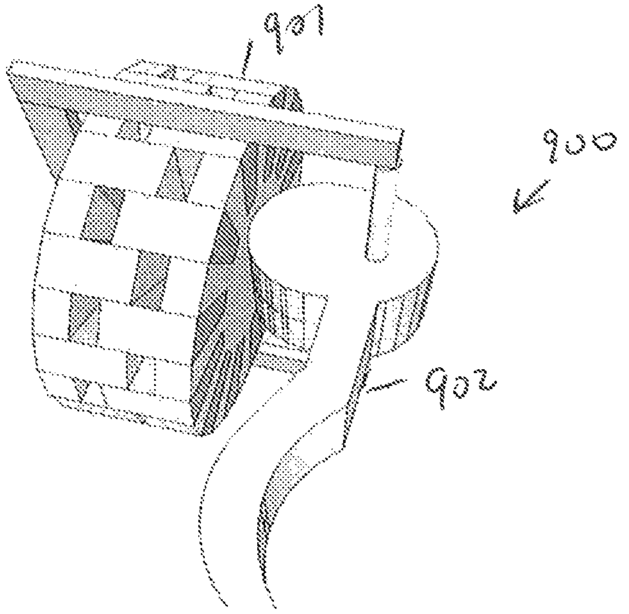
FIG. 11 is a front perspective view of the gear system of the desk and recovery system in a closed position.

FIG. 9 is a perspective side view of the gear system 900 of the desk and recovery system 100 in an open position. FIG. 10 is a front perspective view of the gear system 900 of the desk and recovery system 100 in an open position. FIG. 11 is a front perspective view of the gear system 900 of the desk and recovery system in a closed position. The gear system 900 is located on the pivot points or all parts of the system that rotate. The system features a gear 901 and lever 902. The lever 901 lever secures the gear in a position to prevent movement.

As the the quick release lever 902 is moved from 0 degrees to 180 degrees the distance between the axle and the base of the gear is increased substantially, which locks the gear into place preventing rotation via the teeth on the gear, as shown in FIGS. 9 and 10. The lever is attached to the back of the gear it comes into contact with through magnetic forces so that when you move it from 180 degrees to 0 degrees, the gear moves out with it allowing rotation once again as shown in FIG. 11. For example, the gears are connected to points 601 and 602.

When the rail is rotated to its desired location, the lever locks the gear in position and released when it is desired to adjust its location.

It is preferred that all bases that move in a vertical direction use the pin system described above. However, alternate vertical adjustment systems may be used to adjust the height of the system.

A left and right minor can be attached to the front of the system from the upper body support or head support to afford the user the ability to view surroundings without lifting the head or neck avoiding stress and strain on the head or neck. The mirrors can be attached to mirror arms that allow the length of the arms to be shortened and the mirrors are attached in a manner that they can be adjusted or rotated.

The desk and recovery system can be positioned from left to right such that the buttock support is next to the knee support. The knee support is in between the chest support and buttock support. The adjustable arms are in the front area of the system and support the entertainment system. The system can be reversed from right to left in the same arrangement. Furthermore, the system pivot points can be designed to allow upwards angled positioning of the joints and rails. Alternatively, if the user desires to lie on their back, the system 100 can be structured and positioned so that the upper body support 114 moves in an upwards angled direction. The lower body support 113 can remain in a horizontal position to support the bottom surface of the user's buttocks. The back surface of the user's legs rest on the lower surfaces 112, 111 and the user can position his body in a reclining, standing or fully horizontal position. The supports 110, 120 can be spaced apart a distance described by the user to support the user's body as desired.

In use, a user can lay face down onto the system and remove stress and strain from the user's back but be afforded the ability to be entertained or to work with the objects on the table. The platforms may be removed and the system can be placed directly onto the floor surface and spaced apart to receive users of all heights.

The invention has been described in detail with particular reference to certain preferred embodiments thereof, but it will be understood that variations and modifications can be effected within the spirit and scope of the invention.

The invention claimed is:

1. A recovery system comprising:

a lower body platform;

an adjustable lower body base extending upwards from the lower body platform;

a first and second lower body rail on the lower body base;

pivot points along the lower body rails, a first lower body support on the first and second lower body rail, wherein the first lower body support pivots and moves along the lower body rails, an upper body platform;

an adjustable upper body base extending upwards from the upper body platform;

a knee support on the adjustable upper body base;

a bracket on the adjustable upper body base which supports an upper body support, wherein a front area of the upper body support features rails which receive a head support, wherein the head support is adjustable along the rails.

2. The recovery system of claim 1, further comprising a second lower body support on the first and second lower body rail, wherein the second lower body support moves independently from the first lower body support.

3. The recovery system of claim 1, further comprising an upper body platform;

an adjustable upper body base extending upwards from the upper body platform;

a knee support on the adjustable upper body base;

a bracket on the adjustable upper body base which supports an upper body support, wherein a front area of the upper body support features rails which receive a head support, wherein the head support is adjustable along the rails.

4. The recovery system of claim 1, wherein the upper body support and lower body support move independently from each other.

5. The recovery system of claim 1, wherein arm supports are connected to the bracket on the adjustable upper body base.

6. The recovery system of claim 1, further comprising an opening on the head support, wherein the opening aligns with a first table.

7. The recovery system of claim 1, further comprising a desk platform;
  an adjustable desk base extending upwards from the desk platform;
  at least one arm on the adjustable desk base, wherein the at least one arm features a second table that rotates along the adjustable desk base.

8. The recovery system of claim 1, further comprising a gear system on the pivot points, wherein the gear system features a gear and a lever, whereby the lever secures the gear in a position to prevent movement.

9. A recovery system comprising:
  a lower body platform;
  an upper body platform;
  an adjustable lower body base extending upwards from the lower body platform;
  an adjustable upper body base extending upwards from the upper body platform;
  a first and second lower body rail on the lower body base;
  pivot points along the lower body rails,
  a first lower body support on the first and second lower body rail, wherein the first lower body support pivots and moves along the lower body rails;
  an upper body support on the adjustable upper body base, wherein the lower body support moves independently from the upper body support;
  a gear system on the pivot points, wherein the gear features a gear and a lever,
  whereby the lever secures the gear in a position to prevent movement.

10. The recovery system of claim 9, wherein the adjustable lower body base and adjustable upper body base adjusts in a vertical direction.

11. The recovery system of claim 9, wherein the first and second rail extends horizontally or in an angled position.

12. The recovery system of claim 9, further comprising a gear system on the pivot points, wherein the gear system features a gear and a lever, whereby the lever secures the gear in a position to prevent movement.

13. A recovery system comprising:
  a lower body platform;
  an adjustable lower body base on the lower body platform;
  a first and second lower body rail on the lower body base;
  pivot points along the lower body rails,
  a first lower body support on the first and second lower body rail, wherein the first lower body support pivots and moves along the lower body rails gear system on the pivot points, wherein the gear system secures the rail in a position to prevent movement.

14. The recovery system of claim 13, further comprising an upper body platform;
  an adjustable upper body base on the upper body platform;
  a knee support on the adjustable upper body base;
  a bracket on the adjustable upper body base which supports an upper body support,
  wherein arm supports are connected to the bracket.

15. The recovery system of claim 14, wherein a front area of the upper body support features rails which receive a head support, wherein the head support is adjustable along the rails.

16. The recovery system of claim 13, further comprising a desk platform;
  an adjustable desk base on the desk platform;
  at least one arm on the adjustable desk base, wherein the at least one arm features a table that rotates along the adjustable desk base.

* * * * *